United States Patent

Hashimoto et al.

[11] 4,190,580
[45] Feb. 26, 1980

[54] OPTICALLY ACTIVE MAYTANSINOIDS AND MAYTANSINOID PRODUCTION METHOD

[75] Inventors: Naoto Hashimoto, Suita; Toyokazu Kishi, Nara, both of Japan

[73] Assignee: Takeda Chemical Industries, Ltd., Osaka, Japan

[21] Appl. No.: 948,895

[22] Filed: Oct. 5, 1978

Related U.S. Application Data

[62] Division of Ser. No. 886,815, Mar. 15, 1978, Pat. No. 4,137,230.

[30] Foreign Application Priority Data

Nov. 14, 1977 [JP] Japan ............................ 53/137078
Feb. 20, 1978 [JP] Japan ............................. 53/18675

[51] Int. Cl.² ............................................ C07D 198/18
[52] U.S. Cl. ...................... 260/239.3 P; 260/239.3 T; 424/248.54
[58] Field of Search ................... 260/239.3 P, 239.3 T

[56] References Cited

FOREIGN PATENT DOCUMENTS 1405135  9/1975  United Kingdom ............. 260/239.3 P Primary Examiner—Alan L. Rotman
Assistant Examiner—Robert T. Bond
Attorney, Agent, or Firm—Stevens, Davis, Miller & Mosher

[57] ABSTRACT

Maytansinoid compounds are produced by
(a) treating a compound of the formula

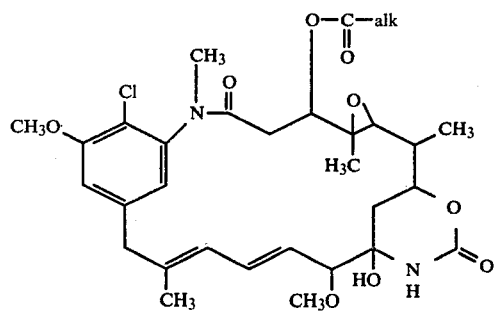

wherein alk is

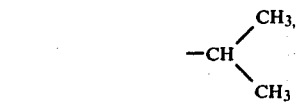

—CH₂CH₂CH₃ or

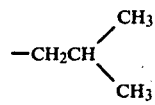

under conditions of reductive hydrolysis to yield maytinsinol; and (b) contacting the maytansinol with an acid of the formula

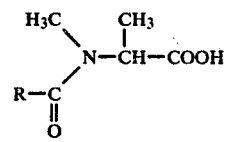

wherein R is lower alkyl, in the presence of a carbodiimide to yield a maytansinoid.

In accordance with a second aspect of the invention there is provided a D-form maytansinoid with respect to the asymmetric center at the 2'-position having the formula:

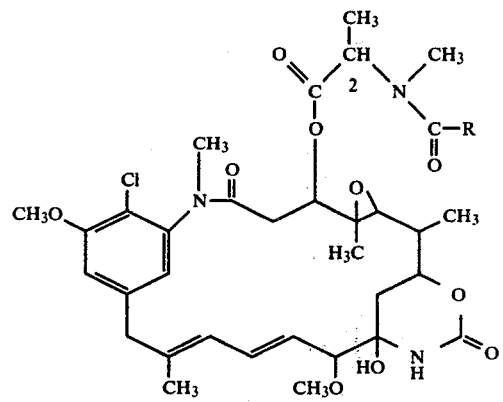

wherein R is a lower alkyl group.

11 Claims, No Drawings

OPTICALLY ACTIVE MAYTANSINOIDS AND MAYTANSINOID PRODUCTION METHOD

CROSS REFERENCE TO RELATED APPLICATION

This application is a division of Ser. No. 886,815, filed Mar. 15, 1978, now U.S. Pat. No. 4,137,230, granted Jan. 30, 1979.

SUMMARY OF THE INVENTION

In a first aspect of the invention, there is provided a method of producing a maytansinoid of the formula:

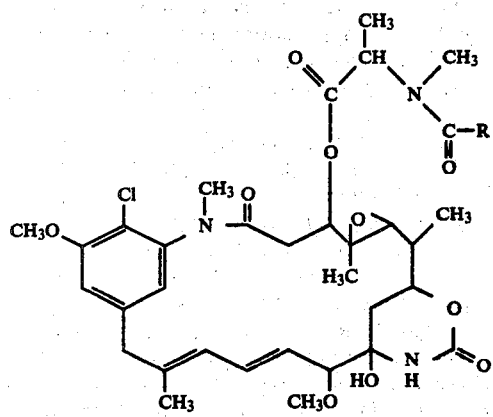

wherein R is lower alkyl, which comprises:
(a) treating a compound of the formula

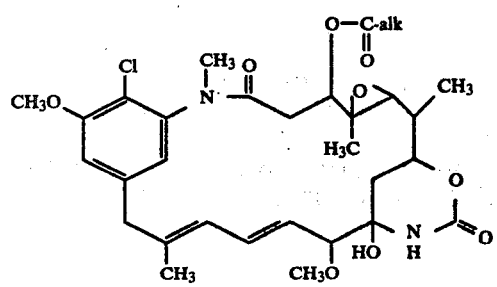

wherein alk is

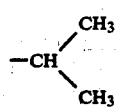

$CH_2CH_2CH_3$ or

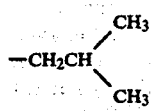

under conditions of reductive hydrolysis to yield maytinsinol; and
(b) contacting the maytansinol with an acid of the formula

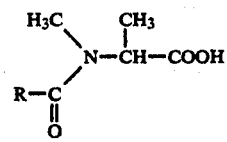

wherein R is lower alkyl, in the presence of a carbodiimide to yield said maytansinoid.

Throughout the specification, the designation "D" or "L" as to the maytansinoid (I) means that the amino acid in the amino acid residue of the maytansinoid (I) is of D- or L-configuration.

The maytansinoid (I) includes the D-form, L-form and a mixture thereof.

Referring to the above formulas (I) and (II), the lower alkyl group R is desirably an alkyl of 1 to 4 carbon atoms such as methyl (L-form: Maytansine), ethyl (L-form: Maytanprine), propyl, isopropyl (L-form: Maytanbutine), butyl, isobutyl (L-form: Maytanvaline), sec-butyl or tert-butyl.

In accordance with a second aspect of the invention there is provided a D-form maytansinoid with respect to the asymmetric center at the 2'-position having the formula:

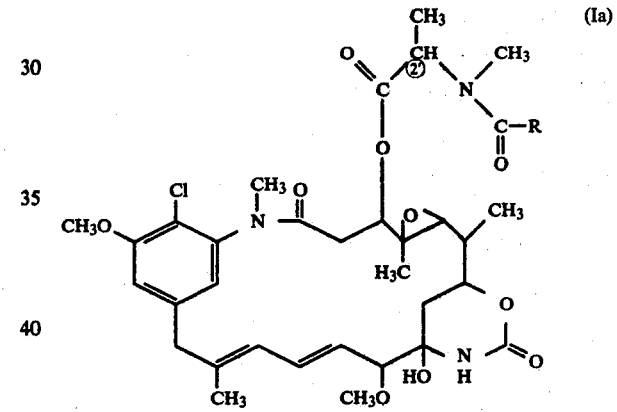

wherein R is a lower alkyl group.

Among the maytansinoids (I), there are known Maytansine, Maytanprine, Maytanbutine and Maytanvaline. The present invention thus provides novel D-form maytansinoids (Ia) and a method for making the L-form or the D-form maytansinoids (I) or a mixture thereof.

The maytansinoids (I) and (Ia) are antifungal agents and also antitumor agents.

DETAILED DESCRIPTION OF THE INVENTION

In the method of this invention, maytansinol is acylated with an acid (II) in the presence of a carbodiimide.

The acid (II) may be any of the L- and D-isomers as well as mixture thereof but where the residue of acid (II) which is to be introduced into the hydroxyl group at the 3-position of maytansinol is an optically active group, it may be desirable to employ the corresponding optically active isomer (II). However, even if an optically active acid (II) is employed, there are cases in which a mixture of L- and L-maytansinoids (I) is obtained according to the reaction conditions employed.

With respect to maytansinol, use may be made of the acid (II) in a proportion of about 1 to 500, preferably up to about 30 molar equivalents, and of the carbodiimide in a proportion of about 1 to 700, preferably up to about 50 molar equivalents.

According to the method of this invention, it is advantageous to conduct the reaction in the presence of a catalyst which may be a suitable acid or base catalyst. As examples of acid catalyst may be mentioned Lewis acids such as anhydrous zinc chloride, anhydrous aluminum chloride (AlCl$_3$), anhydrous ferric chloride, titanium tetrachloride (TiCl$_4$), stannic tetrachloride (SnCl$_4$), antimony pentachloride, cobaltic chloride, cupric chloride, boron trifluoride etherate, etc.; inorganic or organic strong acids such as sulfuric acid, perchloric acid, hydrogen chloride, hydrogen bromide, benzenesulfonic acid, p-toluenesulfonic acid, trifluoroacetic acid, trichloroacetic acid, etc.; acidic ion exchange resins such as Dowex-50 (H+); and so forth. The base catalyst may for example be selected from among organic amine compounds such as pyridine, α-, β- and γ-picoline, 2,6-lutidine, 4-dimethylaminopyridine, dimethylaniline, diethylaniline, triethylamine, N-methylmorpholine, etc.; alkali metal halides such as potassium fluoride, anhydrous lithium iodide, etc.; salts of organic acids such as sodium acetate; and so forth. In many cases, among those catalysts, anhydrous zinc chloride is particularly desirable. The use of such catalyst will result in an improved yield of the maytansinoids (I). The catalyst is employed in an amount sufficient to promote the acylation reaction. Thus, such suitable amount of the catalyst may in many cases be selected from the range of about 0.001 to 10, preferably, from about 0.01 to 1 molar equivalent to acid (II).

Where such a catalyst is employed, an amount of the acid (II) may generally be reduced preferably to about 1 to about 6 molar equivalents to maytansinol.

The carbodiimide of the process of the invention advantageously has the formula:

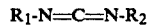

wherein each of R$_1$ and R$_2$ is an organic radical which is capable of permitting the conversion of the carbodiimide portion to the corresponding urea during the reaction of maytansinol and the acid (II). Accordingly, in the generic aspect of this invention, the actual nature of the substitutents R$_1$ and R$_2$ is not of primary importance, with the limitation being present that the substituents permit the conversion of the cardodiimide group to a urea. Although particularly good results have been found using dicyclohexylcarbodiimide, R$_1$ and R$_2$ may also be independently selected from aliphatic and aromatic groups bearing further substituents that permit the conversion of the carbodiimide function to the corresponding urea. R$_1$ and R$_2$ may, for example, be independently cycloalkyl which is unsubstituted or substituted with di-lower alkylamino, lower alkyl which is unsubstituted or substituted with di-lower alkylamino or morpholino, or phenyl which is unsubstituted or substituted with lower alkyl. Some examples of carbodiimides which may be used are diphenylcarbodiimide, di-o-tolylcarbodiimide, di-p-tolylcarbodiimide, di-tert-butylcarbodiimide, etc. as well as 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide, and 1-ethyl-3-(3-dimethylaminopropyl)carbodiimide.

This reaction may be carried out in a suitable solvent such as esters, e.g. ethyl acetate; ethers, e.g. diethylether, dioxane, tetrahydrofuran, etc.; halogenated hydrocarbons, e.g. methylene chloride, chloroform, etc.; nitriles, e.g. acetonitrile; aromatic hydrocarbons, e.g. benzene; nitromethane; pyridine; dimethylformamide; dimethylsulfoxide; sulfolane; etc.; as well as a suitable mixture of such solvents.

This reaction may be conducted, for example at a suitable temperature from ice-cooling up to refluxing temperature of the reaction system.

The compound (I) produced in the above manner can be isolated and purified by routine procedures such as concentration, solvent extraction, chromatography, recrystallization, etc.

By the method of this invention thus far described, maytansinoids can be synthetically and advantageously produced.

The maytansinoids (I) produced in the above manner can be employed in applications similar to applications established for maytansine which is a known compound, for example as carcinostatic or antifungal agents.

Maytansinol may be produced by the method disclosed in Higashide, U.S. Ser. No. 811,448, filed June 29, 1977, which comprises cultivating an Antibiotic C-15003-producing strain in a medium to cause said strain to elaborate and accumulate Antibiotic C-15003 in the culture broth, harvesting the same antibiotic and subjecting it to reductive hydrolysis reaction. It follows, then, that the maytansinoids (I) can be advantageously produced by employing the process of producing maytansinol through a reductive hydrolysis reaction of Antibiotic C-15003 in association with the process of this invention. Incidentally, Antibiotic C-15003 is one of the compounds, or a mixture of two or more of the compounds, which are equivalent to said maytansinoids the 3-substituent of which, however, is either

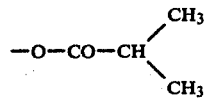

(Antibiotic C-15003 P-3), —O—CO—CH$_2$CH$_2$CH$_3$
(Antibiotic C-15003 P-3') or —O—CO—CH$_2$—

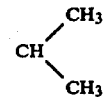

(Antibiotic C-15003 P-4).

A method for making maytansinol and its derivatives is also disclosed in Higashide, U.S. Ser. No. 811,442, filed June 29, 1977.

The acid (II) can be produced by the known method or a method representing a version of said known method. The following is a partial listing of the literature describing such methods:

J. R. Coggins, N. L. Benoiton, Can. J. Chem. 49, 1968(1971), P. Quitt, J. Hellerback, K. Vogler, Helv. Chim. Acta, 46, 327 (1963) and S. L. Portnova, et al, Zh. Obsch. Khim. 38, 428(1968).

Maytansine has been well known to be useful as antifungal agent and also as an agent for treatment of cancers in warm-blooded animals (e.g. mouse, rat, rabbit, dog, cat). Effect of maytansine has been published, for instance, in Kupchan et al. U.S. Pat. No. 3,896,111, Offenlegungsschrift (West Germany) No. 2,241,418, Biochemical Pharmacology, Vol. 24, 751–754(1975), Antimicrobial Agents and Chemotherapy, Vol. 6, No. 5, 651–652(1974).

Maytansinoids (I) produced by the present method can be useful in similar ways to those for maytansine. Maytansinoids (I) can be administered parenterally by subcutaneous, intraperitoneal or intravenous route at a suitable dose of about 1.0 µg/kg body weight to about 50 µg/kg body weight per one administration to produce prolongation of survival of warm-blooded animals (e.g. mouse, rat) bearing cancers. Injection solution may be prepared by known method, for instance, by dissolving maytansinoid (I) in ethanol and adding physiological saline to the ethanol solution.

As mentioned hereinbefore, the present maytansinoid (I) has strong inhibitory activity against fungi and protozoa and, therefore, is of value as an antifungal or antiprotozoan agent.

Maytansinoid (I), as an antifungal and antiprotozoan agent, can be used with advantage for an assessment of the bacterial ecology in the soil, active sludge, animal body fluid or the like. Thus, when valuable bacteria are to be isolated from soil samples or when the actions of bacteria are to be evaluated independently of those of fungi and protozoa in connection with the operation and analysis of an active sludge system used in the treatment of waste water, as the maytansinoid (I) may be utilized to obtain a selective growth of the bacterial flora without permitting growth of the concomitant fungi and protozoa in the specimen. In a typical instance, the sample is added to a liquid or solid medium and 0.1 ml of a 10 to 100 µg/ml solution of the maytansinoid (I) in 1% methanol-water is added per ml of the medium, which is then incubated.

The present maytansinoid (I) can also be used as an anti-microbial agent for the treatment of plant diseases caused by various microorganisms.

In the typical application, maytansinoid (I) is used in a form of 1% methanolic aqueous solution containing about 0.5 µg/ml–about 5 µg/ml of the maytansinoid (I). For instance maytansinoid (I) may be used for the control of the reddish brown sheath rot, the blast, the Helminthosporium leaf spot and the sheat blight of rice plants.

In the following Examples, silica gel used for column-chromatography is the commercial product of Kieselgel 60, Art 7734 of Merck, West Germany unless otherwise referred to.

EXAMPLE 1

In round-bottomed flask of 50 ml capacity were placed 47.3 mg (0.0837 mmol) of maytansinol and 145 mg (1.0 mmol) of N-methyl-N-acetyl-L-alanine. On addition of 10 ml of anhydrous methylene chloride, a homogeneous solution was obtained. To this solution was added 10 ml of solution of 309 mg (1.5 mmol) of dicyclohexylcarbodiimide in anhydrous dichloromethane, whereupon colorless crystals separated immediately. Under stirring, this suspension was refluxed on an oil bath at a bath temperature of 55°–60° C. for 10 hours. After the reaction had been completed, the reaction mixture was concentrated under reduced pressure and the insolubles were separated by filtration. The insolubles were washed with a small quantity of methylene chloride and the washings were combined with the filtrate. The combined filtrate was concentrated under reduced pressure and the residue was chromatographed on a column packed with 40 g of silica gel with chloroform-methanol=45:1 v/v. The forerun containing the by-product dicyclohexylurea as a predominant solute was discarded and bioautographically positive fractions (see bioautographic test described hereinafter) were pooled. From the rear run from the column, 27 mg of maytansinol was recovered.

The bioautographically active fractions were combined, concentrated and chromatographed on a column packed with 27 g of silica gel, elution being carried out with ethyl acetate methyl acetate saturated with water (2:1). By this procedure, 7.0 mg of a colorless bioautographically active compound was isolated. This product was confirmed to be a single compound by thin-layer chromatography on a TLC plate (Kieselgel 60 $F_{254}$, Art 5715, Merck, West Germany) in two solvent systems of chloroform-methanol (9:1 v/v) and ethyl acetate saturated with water.

Based, in part, on the data given hereinafter, the structure of this compound was confirmed to be (I) ($R=CH_3$).

Elemental analysis, for $C_{34}H_{46}ClN_3O_{10}$: Calcd. C, 59.00; H, 6.70; N, 6.07: Found C, 58.68; H, 7.02; N, 6.54.

Mass spectrum(in $CHCl_3$) m/e: 691 ($M^+$, trace), 630 ($M^+-H_2O-HNCO$), 485, 470, 450.

UV spectrum(in EtOH) max (nm): 233, 243, 254, 282, 290.

Bioautographic test used in the present Examples

*Talaromyces avellanens* (IFO 7721) was inoculated on 1% glucose bouillon agar slants and, on the 4th day, one of the slants was admixed with an assay medium (pH 7.1) composed of 3.5 g/l $Na_2HPO_4.H_2O$ (in distilled water), 0.5 g of $KH_2PO_4$, 5.0 g of yeast extract (Difco), 10 g of glucose and 15 g of agar at 50° C. 20 ml portions of the mixture were distributed into dishes (7.5×22.5 cm) and stored in the cold. Then, a filter paper or TLC plate imbibed with the test sample was held tightly on the agar plate in each dish for a predetermined time. After the filter paper or TLC plate was removed, incubation was carried out at 37° C. and the zone of inhibition was measured.

EXAMPLES 2 TO 9

The following stock solutions were prepared:

Solution A=A solution of maytansinol in anhydrous methylene chloride, containing 1 mg of maytansinol in 50 mcl of the solution.

Solution B=A solution of dicyclohexylcarbodiimide in anhydrous methylene chloride, containing 6 mg of dicyclohexylcarbodiimide in 50 mcl of the solution.

Solution C=A solution of N-acetyl-N-methyl-L-alanine in anhydrous methylene chloride containing N-acetyl-N-methyl-L-alanine in a concentration of 3 mg/50 ml of the solution.

In a glass tube about 4 mm across and about 14 cm long, 50 mcl of Solution C, 50 mcl of Solution B and 50 mcl of Solution A were taken in that order by means of a syringe and admixed. Then, a catalyst, either as it was in the case of a solid catalyst or as previously diluted with anhydrous methylene chloride to a suitable concentration where it was a liquid catalyst, was added (amount of catalyst approx. 0.3 mg). Finally, the reaction mixture was adjusted to 200 mcl each with methylene chloride. The glass tube was sealed by melting at about 12 cm along its length and, with occasional shaking, the tube was allowed to stand at the indicated temperature for 14 hours. The tube was then unsealed and 2 mcl aliquots of the contents were applied to TLC plates (silica gel 60 $F_{254}$, Art 5715, 20 cm×20 cm, Merck, West Germany). After development with chloroform-methanol (9:1 by v/v), the maytansine spot was detected by Shimadzu Chromatoscanner CS-910 at a detection wavelength of 250 nm and a reference wavelength of 350 nm and the absolute and percent yields of maytansine were calculated against the calibration curve previously prepared. When there was a recovery of maytansinol, the percent recovery was similarly determined at the same time.

| Ex. | Catalyst | Reaction temperature (°C.) | Yield of maytansine (%) | Recovery of maytansinol (%) |
|---|---|---|---|---|
| 2 | Anhydrous zinc chloride | 15–25 | 70 | 15 |
| 3 | Anhydrous zinc chloride | 0–5 | 80 | 15 |
| 4 | Anhydrous aluminum chloride | 15–25 | 20 | 0 |
| 5 | Titanium tetrachloride | 15–25 | 15 | 0 |
| 6 | Anhydrous ferric chloride | 15–25 | 6 | 0 |
| 7 | Stannic tetrachloride | 15–25 | 35 | 50 |
| 8 | Boron trifluoride etherate | 15–25 | 27 | 5 |
| 9 | Sulfuric acid | 15–25 | 32 | 3 |

EXAMPLES 10 TO 12

To mixtures of 50 mcl each solutions C, B and A as prepared in glass tubes in the same manner as in Examples 2 to 9, about 2 mg of the catalyst was added and the reaction was conducted as in Examples 2 to 9. Then maytansine produced was quantitatively determined similarly. The percent recoveries of maytansinol were also determined at the same time.

| Example | Catalyst | Yield of maytansine (%) | Recovery of maytansinol (%) |
|---|---|---|---|
| 10 | Anhydrous potassium fluoride | 30 | 55 |
| 11 | Anhydrous lithium iodide | 30 | 20 |
| 12 | 4-Dimethylaminopyridine | 25 | 35 |

EXAMPLE 13

In 20 ml of anhydrous methylene chloride was dissolved 159 mg of N-methyl-N-propionyl-L-alanine, followed by addition of 309 mg of dicyclohexylcarbodiimide and 48 mg of maytansinol. The mixture was heated under reflux and to the exclusion of moisture for 16 hours. The reaction mixture was concentrated and the insolubles were filtered off. The filtrate was concentrated under reduced pressure and the residue was run onto a column packed with 40 g of silica gel. Development was carried out with chloroform-methanol (45:1 v/v) and bioautographically positive fractions were pooled. The solvent was distilled off and the residue was rechromatographed on a column of silica gel (27 g of silica gel; developing solvent: ethyl acetate-ethyl acetate saturated with water=2:1 v/v). The bioautographically positive fractions were collected to recover 5 mg of a colorless compound. This product was identified as compound (I) (R=$C_2H_5$) in the same manner as in Example 1.

Mass Spectrum (m/e): 644 ($M^+$-61), 485, 470

EXAMPLE 14

By a procedure similar to that described in Example 13, 173 mg of N-isobutyryl-N-methyl-L-alanine, 309 mg of dicyclohexylcarbodiimide and 48 mg of maytansinol were reacted in 20 ml of anhydrous methylene chloride. The reaction mixture was further treated as in Example 13 to recover 3.2 mg of a colorless compound. Based on its mass spectrum, this product was identified with compound

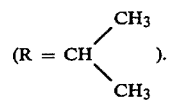

Mass spectrum (m/e): 658 ($M^+$-61), 485, 470

EXAMPLE 15

By a procedure similar to that set forth in Example 13, 187 mg of N-methyl-N-isovaleryl-L-alanine, 309 mg of dicyclohexylcarbodiimide and 48 mg of maytansinol were reacted in 20 ml of anhydrous methylene chloride. The reaction mixture was treated as in Example 13 to recover 2.5 mg of a colorless compound. Based on its mass spectrum, this product was identified as compound (I) (R=$CH_2CH(CH_3)_2$).

Mass spectrum (m/e): 672 ($M^+$-61), 485, 470

EXAMPLE 16

Maytansinol (300 mg, 0.5315 mmol) and N-acetyl-N-methyl-L-alanine (1.585 g, 10.62 mmol) were dissolved in 80 ml of dichloromethane. To this were added 3.285 g of dicyclohexylcarbodiimide and 72.5 mg (0.532 mmol) of anhydrous zinc chloride. The mixture was stirred at ca. 20° C. for 6 hours and allowed to stand at the same temperature for 11 hours. Then, N-acetyl-N-methyl-L-alanine (530 mg), dicyclohexylcarbodiimide (1095 mg) and anhydrous zinc chloride (150 mg) were further added. After two hours, the reaction mixture was filtered and the filtrate was washed with ca. 150 ml of water and dried over anhydrous sodium sulfate. The insolubles were filtered off and the filtrate was chromatographed on a column of silica gel (60 g) with chloroform/methanol=40/1 (v/v), collecting—after some forerun having been cut —25-g fractions. Fractions 14–25 were combined, concentrated and rechromatographed using 65 g of silica gel with ethyl acetate/ethyl acetate saturated with water=2/1 (v/v), collecting—after some forerun—16-g fractions to give 149.3 mg of compound (I) (R=$CH_3$) (Compound A) from fractions 25–60. Fractions 23,24 and 61–100 from the second chromatography were combined and evaporated to give 20.5 mg os substance from which another crop (6.3 mg) of Compound A was recovered by subjecting it to preparative thin-layer-chromatography on silica gel (Kieselgel 60 $F_{254}$, Art 5717, Merck, West Germany) with 10% isopropanol-chloroform. Fractions 101–153 of the second chromatography were combined and concentrated to give 320 mg of a product from which 95.7 mg of an isomer of Compound (I) (R=$CH_3$) (Compound B) was obtained upon re-chromatography on a column of silica gel (75 g) with chloroform/methanol=40/1 (v/v). Total yield of Compound A was 155.6 mg and that of Compound B was 95.7 mg.

Compound A was identified with the natural Maytansine by comparing the following data of Compound A with those of natural Maytansine described in Journal of Organic Chemistry, 42, No. 14,2349-2357 (1977).

UV-spectrum($\lambda$max, EtOH) nm: 289, 281, 254, 242(sh), 233

NMR-spectrum(in CDCl$_3$) $\delta$: 0.79(3H,s), 1.27(3H,d,J=4 Hz), 1.29(3H,d,J=7 Hz), 1.63(3H,s), 2.10(3H,s), 2.12(1H, dd, J=3 Hz and 15 Hz), 2.62(1H,dd,J=12 Hz and 15 Hz), 2.84(1H,s), 3.02(1H,d,J=9 Hz), 3.07(1H,d,J=13 Hz), 3.18 (3H,s), 3.34(3H,s), 3.45(1H,d,J=9 Hz), 3.64(1H,d,J=13 Hz), 3.96(3H,s), 4.25(1H,m), 4.75(1H,dd,J=3 Hz and 12 Hz), 5.37(1H,q,J=7 Hz), 5.64(1H,dd,J=9 Hz and 15 Hz), 6.37(1H,s), 6.37(1H,dd,J=11 Hz and 15 Hz), 6.68(1H,d,J=11 Hz), 6.73(1H,s), 6.80(1H,s), 0.80-2.50(3H), 3.90(1H,s).

Mass spectrum (m/e): 691, 630, 485, 470, 450, 128, 100, 58 $[\alpha]_D^{23}-136°\pm30°$(c=0.055, CHCl$_3$).

Compound B was identified with an isomer of Maytansine which is considered to the D-Maytansine by comparing the following data of Compound B with those of Maytansine.

UV-spectrum($\lambda$max, EtOH) nm: 289, 281, 253, 240(sh), 233

NMR-spectrum(in CDCl$_3$) $\delta$: 0.78(3H,s), 1.26(3H,d,J=4 Hz), 1.49(3H,d,J=7.5 Hz), 1.69(3H,s), 2.15(3H,s), 2.17 (1H,dd,J=3 Hz and 14 Hz), 2.68(1H,dd,J=12 Hz and 14 Hz), 2.82(1H,d,J=9 Hz), 3.03(3H,s), 3.15(3H,s), 3.18(1H,d,J=12 Hz), 3.34(3H,s), 3.42(1H,d,J=9 Hz), 3.49(1H,d,J=12 Hz); 3.98(3H,s), 4.27(1H,m), 4.84(1H,dd, J=3 Hz and 12 Hz), 5.01(1H,q,J=7 Hz), 5.51(1H,s), 5.83(1H,dd,J=9 Hz and 14 Hz), 6.17(1H,d,J=11 Hz), 6.23(1H,s), 6.44(1H,dd,J=11 Hz and 14 Hz), 6.77(1H,s), 6.83(1H,s), 0.80-2.30(3H).

Mass spectrum (m/e): 691, 630, 485, 470, 450, 128, 100, 58 $[\alpha]_D^{23}-129°\pm30°$(c=0.055, CHCl$_3$)

EXAMPLE 17

Maytansinol (100 mg, 0.177 mmol) and N-acetyl-N-methyl-L-alanine (522 mg, 3.59 mmol) were dissolved in 25 ml of dichloromethane. To this, under cooling with an ice-water bath at the temperatures below 5° C., were added 1100 mg (5.38 mmol) of dicyclohexylcarbodiimide and 24 mg of anhydrous zinc chloride. The mixture was stirred at below 5° C. for 20 hours, then filtered. The filtrate was concentrated and the residue was subjected to silica gel column chromatography (55 g), with chloroform/methanol=40/1 (v/v), collecting 25-g fractions. Fractions 15-30 were combined and evaporated to give 147 mg of a mixture of materials. From fractions 31-200, 43 mg of maytansinol was recovered.

The 147 mg-product was subjected to the 2nd column chromatography with ethyl acetate/ethyl acetate saturated with water=2/1 (v/v). Some forerun was discarded and then the eluate was collected in 15-g fractions, to give 34 mg of Maytansine, 17 mg of a mixture of Maytansine and some other substances and 47 mg of substance containing an isomer of Maytansine. Preparative thin-layer-chromatography (PLC plate, silica gel 60F$_{254}$, Art 5717, Merck, West Germany) with methylene chloride/isopropanol=9:1 of the 17 mg product gave another crop (5.0 mg) of Maytansine. The 47 mg-product was further chromatographed on a column of silica gel (60 g) with chloroform/ethanol=40/1 (v/v) to give 20.0 mg of the isomer of Maytansine. The total yields of Maytansine and the isomer of Maytansine were 39 mg and 20 mg, respectively.

Maytansine and its isomer prepared above showed the same UV, NMR and Mass spectra as in Example 16.

EXAMPLE 18

Maytansinol (100 mg, 0.177 mmol), N-methyl-N-propionyl-L-alanine (84.5 mg, 0.531 mmol) and dicyclohexylcarbodiimide (164 mg, 0.796 mmol) were dissolved in 15 ml of dry dichloromethane. A suspension with white precipitate formed immediately. To this was added under stirring at room temperature ca. 24 mg (0.176 mmol) of anhydrous zinc chloride. After one hour's stirring at the same temperature, N-methyl-N-propionyl-L-alanine (84.5 mg), dicyclohexylcarbodiimide (164 mg) and anhydrous zinc chloride (ca. 24 mg) and 10 ml of dichloromethane were further added and the mixture was further stirred for another one hour and fifty minutes. Then, the reaction mixture was filtered to remove small amount of insoluble material and the filtrate was diluted with dichloromethane to a volume of ca. 100 ml, washed with water, dried over anhydrous sodium sulfate and then filtered. The filtrate was concentrated under reduced pressure and the precipitate separated was filtered and washed with small amount of ethyl acetate. The combined filtrate and washings was chromatographed on a column of silica gel (65 g) with ethyl acetate/ethyl acetate saturated with water=2/1 (v/v), collecting, after some forerun having been cut, 15-g fractions. Fractions 7-31 were combined, evaporated to give 66 mg of compound (I) (R=C$_2$H$_5$) (Compound C) and from fractions 40-97, 58 mg of an isomer of compound (I) (R=C$_2$H$_5$) (Compound D) was obtained.

Compound C was identified with the natural Maytanprine by comparing the NMR- and mass-spectra of the former with those of tha latter compound in the literature cited in the Example 16.

NMR-spectrum(in CDCl$_3$) $\delta$: 0.80(3H,s), 1.10(3H,t,J=7 Hz), 1.27(3H,d,J=4 Hz), 1.29(3H,d,J=7 Hz), 1.64(3H,s), 2.15(1H,dd,J=14 Hz and 3 Hz), 2.33(2H,m), 2.61(1H,dd,J=14 Hz and 12 Hz), 2.82(3H,s), 3.01(1H,d,J=9 Hz), 3.18(3H,s), 3.33(3H,s), 3.48(1H,d,J=9 Hz), ~3.60 (1H,br), 3.65(1H,d,J=13 Hz), 3.96(3H,s), 4.26(1H,m), 4.76(1H,dd,J=12 Hz and 3 Hz), 5.40(1H,q,J=7 Hz), 5.66(1H,dd,J=15 Hz and 9 Hz), 6.30(1H,br.s), 6.40(1H,dd,J=15 Hz and 11 Hz), 6.65(1H,d,J=1.5 Hz), 6.74 (1H,d,J=11 Hz), 6.80(1H,d,J=1.5 Hz), 0.8-2.5(3H), 3.09(1H,d,J=13 Hz).

Mass spectrum (m/e): 644, 485, 470, 450, 142

Compound D was identified with an isomer of Maytanprine which is considered to be D-Maytanprine by comparing the following data of Compound D with those of Maytanprine.

NMR-spectrum(in CDCl$_3$) $\delta$: 0.86(3H,s), 1.13(3H,t,J=7 Hz), 1.26(3H,d,J=4 Hz), 1.49(3H,d,J=7 Hz), 1.69(3H,s), 2.17(1H,dd,J=15 Hz and 3 Hz), 2.40(2H,q,J=7 Hz), 2.67(1H,dd,J=15 Hz and 12 Hz), 2.81(1H,d,J=9 Hz), 3.01(3H,s), 3.15(3H,s), 3.16(1H,d,J=13Hz), 3.33(3H, s), 3.44(1H,d,J=9 Hz), 3.50(1H,d,J=13 Hz), 3.97(3H,s), 4.28(1H,m), 4.88(1H,dd,J=12 Hz and 3 Hz), 5.09(1H,q,J=7 Hz), 5.84(1H,dd,J=14 Hz and 9 Hz), 6.20(1H,d,J=11 Hz), 6.25(1H,br.s), 6.44(1H,dd,J=14 Hz and 11 Hz), 6.79(1H,d,J=1.5 Hz), 6.84(1H,d,J=1.5 Hz), ~4.96(1H,s), 0.8-2.2(3H).

Mass spectrum (m/e): 705, 644, 485, 470, 450, 142, 114

EXAMPLE 19

Maytansinol (100 mg, 0.177 mmol), N-isobutyryl-N-methyl-L-alanine (92 mg, 0.532 mmol), and dicyclohexylcarbodiimide (164 mg, 0.796 mmol) were dissolved in 15 ml of dry dichloromethane. To this, under cooling in an ice-water bath and under stirring, 24 mg of anhydrous zinc chloride was added and the mixture was stirred for half an hour under ice-cooling. Then, the ice-water bath was removed and the reaction mixture was warmed up to room temperature (ca. 20° C.). After further one hour, N-isobutyryl-N-methyl-L-alanine (92 mg), dicyclohexylcarbodiimide (164 mg) and anhydrous zinc chloride (ca. 24 mg) were added together with 10 ml of dry dichloromethane. And, after further 45 minutes, N-isobutyryl-N-methyl-L-alanine (31 mg), dicyclohexylcarbodiimide (55 mg) and anhydrous zinc chloride (ca. 24 mg) were further added and the reaction mixture was further stirred for another 45 minutes. Total reaction time was 3 hours. Then, the reaction mixture thus obtained was worked up as in Example 17 and the material obtained was chromatographed on a silica gel (65 g) with ethyl acetate/ethyl acetate saturated with water=2/1 (v/v), collecting 15-g fractions as in Example 17. Fractions 8-22 were combined and the solvent was evaporated to give 70.5 mg of compound (I) (R=CH(CH$_3$)$_2$) (Compound E). And, fractions 27-55 gave, after combining and evaporation of solvent, 57.5 mg of an isomer of compound (I) (R=CH(CH$_3$)$_2$) (Compound F).

Compound E was identified with the natural Maytanbutine by comparing the following data of Compound E with those of natural Maytanbutine described in the literature cited in the Example 16.

NMR-spectrum(in CDCl$_3$) δ: 0.80(3H,s), 1.09(6H,t,J=7 Hz), 1.28(3H,d,J=4 Hz), 1.28(3H,d,J=6 Hz), 1.64(3H,s), 2.13(1H,dd,J=14 Hz and 3 Hz), 2.61(1H,dd,J=14 Hz and 12 Hz), 2.81(0.63H,s), 2.87(2.37H,s), ~2.85(1H,m), 2.99(1H,d,J=9 Hz), 3.06(1H,d,J=13 Hz), 3.16(3H,s), 3.36(3H,s), 3.49(1H,d,J=9 Hz), 3.68(1H,d,J=13 Hz), ~3.80(1H,br.), 3.96(3H,s), 4.27(1H,m), 4.75(1H,dd,J=12 Hz, and 3 Hz), 5.43(1H,q,J=7 Hz), 5.66(1H,dd,J=15 Hz and 9 Hz), 6.36(1H,br.s), 6.42(1H,dd,J=15 Hz and 11 Hz), 6.65(1H,d,J=1.5 Hz), 6.79(1H,d,J=1.5 Hz), 6.80(1H,d,J=11 Hz), 0.7-2.1(3H).

Mass spectrum (m/e): 719, 658, 485, 470, 450, 156

Compound F was identified with an isomer of Maytanbutine which is considered to be D-Maytanbutine by comparing the following data of Compound F with those of Maytanbutine.

NMR-spectrum(in CDCl$_3$) δ: 0.86(3H,s), 1.13(6H,d,J=6 Hz), 1.27(1H,d,J=4 Hz), 1.49(3H,d,J=7 Hz), 2.17(1H,dd,J=15 Hz and 3 Hz), 2.66(1H,dd,J=15 Hz and 12 Hz), 2.80(1H,d,J=9 Hz), ~2.90(1H,m), 3.05(3H,s), 3.15 (3H,s), 3.18(3H,d,J=13 Hz), 3.33(3H,s), 3.42(1H,d,J=9 Hz), 3.50(1H,d,J=13 Hz), 3.98(3H,s), 4.29(1H,m), 4.90(1H,dd,J=12 Hz and 3 Hz), 5.08(1H,q,J=7 Hz), 5.13 (1H,s), 5.84(1H,dd,J=14 Hz and 9 Hz), 6.20(1H,d,J=11 Hz), 6.25(1H,br.s), 6.44(1H,dd,J=14 Hz and 11 Hz), 6.78(1H,d,J=1.5 Hz), 6.84(1H,d,J=1.5 Hz), 0.75-2.5(3H).

Mass spectrum (m/e): 719, 658, 485, 470, 450, 156

EXAMPLE 20

Maytansinol (100.5 mg, 0.1779 mmol) was treated as in Example 17 at room temperature (ca. 20° C.) with, firstly, N-isovaleryl-N-methyl-L-alanine (99.5 mg, 0.532 mmol), dicyclohexylcarbodiimide (165 mg, 0.801 mmol), and anhydrous zinc chloride (ca. 24 mg) in dry dichloromethane (15 ml) for one hour, and then secondly with N-isovaleryl-N-methyl-L-alanine (67 mg, 0.358 mmol), dicyclohexylcarbodiimide (110 mg, 0.534 mmol) and anhydrous zinc chloride (ca. 24 mg) and dry dichloromethane (10 ml) for further one hour. The reaction mixture thus obtained was worked up as in Example 17 and the crude product thus obtained was chromatographed on a column of silica gel (65 g) with ethyl acetate collecting 15-g fractions, after some fore-run having been discarded. Fractions 17-29 were combined and the solvent was evaporated to give 60 mg of compound (I) (R=CH$_2$CH(CH$_3$)$_2$) (Compound G). Fractions 33-75 gave, after combining and evaporation of solvent, 57 mg of an isomer of compound (I) (R=CH$_2$CH(CH$_3$)$_2$) (Compound H).

Compound G was identified with the natural Maytanvaline by comparing the NMR- and mass-spectra of Compound G with those of Maytanvaline.

NMR-spectrum(in CDCl$_3$) δ: 0.79(3H,s), 0.91(3H,d,J=6 Hz), 0.95(3H,d,J=6 Hz), 1.27(3H,d,J=6 Hz), 1.30(3H,d,J=7 Hz), 1.64(3H,s), 2.13(2H,d,J=7 Hz), 2.15(1H,dd,J=14 Hz and 3 Hz), 2.60(1H,dd,J=14 Hz and 11 Hz), 2.83(3H,s), 3.00(1H,d,J=9 Hz), 3.07(1H,d,J=13 Hz), 3.17(3H,s), 3.34(3H,s), 3.47(1H,d,J=9 Hz), 3.59(1H,br.), 3.65(1H,d,J=13 Hz), 3.95(3H,s), 4.27(1H,m), 4.74(1H,dd,J=12 Hz and 3 Hz), 5.35(1H,q,J=7 Hz), 5.64(1H,dd,J=15 Hz and 9 Hz), 6.28(1H,br.s), 6.39(1H,dd,J=15 Hz and 11 Hz), 6.67(1H,d,J=2 Hz), 6.69(1H,d,J=11 Hz), 6.79(1H,d,J=2 Hz), 0.7-2.0(3H).

Mass spectrum (m/e): 733, 672, 485, 470, 450, 170

Compound H was identified with an isomer of Maytanvaline which is considered to be D-Maytanvaline by comparing the following data of Compound H with those of Maytanvaline.

NMR-spectrum(in CDCl$_3$) δ: 0.89(3H,s), 0.93(3H,d,J=6 Hz), 0.96(3H,d,J=6 Hz), 1.26(3H,d,J=4 Hz), 1.49(3H,d,J=7 Hz), 1.69(3H,s), 2.66(1H,dd,J=15 Hz and 12 Hz), 3.02(3H,s), 3.12(3H,s), 3.18(1H,d,J=13 Hz), 3.32 (3H, s), 3.42(1H,d,J=9 Hz), 3.50(1H,d,J=13 Hz), 3.96(3H,s), 4.29(1H,m), 4.92(1H,dd,J=11 Hz and 3 Hz), 5.00(1H,q, J=7 Hz), 5.05(1H,br.), 5.78(1H,dd,J=15 Hz and 9 Hz), 6.17(1H,d,J=11 Hz), 6.43(1H,dd,J=15 Hz and 11 Hz), 6.77(1H,d,J=1.5 Hz), 6.83(1H,d,J=1.5 Hz), 0.8-2.5 (7H), 6.24(1H,s).

Mass spectrum (m/e): 733, 672, 485, 470, 450, 170

EXAMPLE 21

Maytansinol (100.0 mg, 0.177 mmol), N-acetyl-N-methyl-DL-alanine (64.5 mg, 0.443 mmol, 2.5 mol. eq.) and dicyclohexylcarbodiimide (109.5 mg, 0.532 mmol, 3.0 mol. eq.) were dissolved in 20 ml of dry dichloromethane. To this was added under stirring at room temperature ca. 24 mg (0.177 mmol, 1.0 mol. eq.) of anhydrous zinc chloride. After 30 minutes' stirring at the same temperature, N-acetyl-N-methyl-DL-alanine (51.5 mg, 0.354 mmol, 2.4 mol. eq.) and anhydrous zinc chloride (ca. 24 mg, 1.0 mol. eq.) were further added and the reaction mixture was stirred for further one hour. Then, 80 ml of dichloromethane and 20 ml of water were added. The organic layer was separated and dried over anhydrous sodium sulfate, then filtered. The filtrate was evaporated to dryness and to the residue, 3 ml of ethyl acetate was added and some insolubles were filtered off. The filtrate was concentrated and chromatographed on a column of silica gel (60 g) with ethyl acetate. Fractions which show TLC-spot corresponding to each Compound A and Compound B, respectively were combined—separately—and the solvent was evaporated to give 60 mg of Compound A and 60 mg of Compound B, respectively. Both Compound A (Maytansine) and Compound B (supposed to be D-Maytansine) thus obtained were identified with those products obtained in Example 16 by the comparison of NMR-spectrum. Rf-Values of Maytansinoids (I) on Thin-Layer-Chromatography On the TLC-Plate(Art. 5715, Merck, West Germany)

| Compound No. | Solvent system | Rf-values $CHCl_3$/methanol $=9/1(v/v)$ | Ethyl acetate saturated with water |
|---|---|---|---|
| A | | 0.28 | 0.15 |
| B | | 0.28 | 0.05 |
| C | | 0.32 | 0.24 |
| D | | 0.37 | 0.18 |
| E | | 0.35 | 0.29 |
| F | | 0.42 | 0.19 |
| G | | 0.39 | 0.35 |
| H | | 0.48 | 0.24 |
| (Maytansinol) | | 0.11 | 0.16 |

EXAMPLE 22

In 600 ml of methanol was suspended 53.5 g (0.52 mol) of N-methyl-L-alanine and under ice-cooling and stirring, 75 g of dry hydrogen chloride gas was dissolved. The suspension of the starting material cleared gradually with reaction time and, on stirring overnight, yielded a homogeneous solution. To the reaction mixture was added 85 g (0.8 mol) of methyl orthoformate and the mixture was allowed to stand at room temperature for 24 hours. The small quantities of insolubles were filtered off and the filtrate was concentrated under reduced pressure. By the above procedure was obtained a solid product of N-methyl-L-alanine methyl ester hydrochloride.

NMR spectrum(DMSO-$d_6$) δ: 1.50(3H,d,J=7 Hz), 2.60(3H,m; after addition of deuterium oxide, s), 3.75(3H,s), 4.12 (1H,m; after addition of deuterium oxide, q,J=7 Hz), 9.83(2H,br.)

EXAMPLE 23

In 300 ml of chloroform was dissolved 33.7 g (0.22 mol) of N-methyl-L-alanine methyl ester hydrochloride, followed by addition of 65 ml of acetic anhydride and 110 ml of triethylamine. The mixture was allowed to stand at room temperature for 24 hours and, after the excess acetic anhydride was decomposed with water, the solution was neutralized with sodium bicarbonate. The chloroform layer was separated and the water layer was extracted with ethyl acetate (120 ml×5). The chloroform and ethyl acetate layers were combined and concentrated under reduced pressure. The brown-colored oily residue was dissolved in chloroform and washed with an aqueous solution of sodium hydrogen carbonate, followed by concentration under reduced pressure. By the above procedure was obtained 31.8 g of N-acetyl-N-methyl-L-alanine methyl ester.

NMR spectrum(CDCl$_3$) δ: 1.38(3H,d,J=7 Hz), 2.12(3H,s), 2.97(3H,s), 3.70(3H,s), 5.23(1H,q,J=7 Hz)

The ester thus obtained was dissolved in 100 ml methanol-170 ml 1 N-aqueous sodium hydroxide and the solution was allowed to stand at room temperature for 2 hours. The methanol was removed under reduced pressure and the alkaline aqueous solution was extracted with chloroform. The water layer was adjusted to pH 1 with concentrated hydrochloric acid under ice-cooling and extracted with ethyl acetate (140 ml×5). The extract was dried over anhydrous sodium sulfate and concentrated under reduced pressure. The resultant white solid was recrystallized from ethyl acetate-hexane. By the above procedure was obtained 8.1 g colorless needles of N-acetyl-N-methyl-L-alanine.

Elemental analysis, for $C_6H_{11}NO_3$: Calcd. C, 49.64; H, 7.64; N, 9.65: Found C, 49.54; H, 7.66; N, 9.40. $[\alpha]_D^{25} -58.5°(c=1, DMF) -74.3°(c=1, H_2O)$
m.p. 121°-122° C.

NMR spectrum(CDCl$_3$) δ: 1.42(t, J=7 Hz) & 1.50(t,J=7 Hz), total 3H; 2.12(3H,s); 2.88(s) & 2.98(s) total 3H; 4.53(q,J=7 Hz) & 5.25 (q, J=7 Hz) total 1H; 11.38(1H,s).

EXAMPLE 24

In 150 ml of chloroform was dissolved 28 g (0.18 mol) of N-methyl-L-alanine methyl ester hydrochloride, followed by addition of 27 g (0.21 mol) of propionic anhydride and 33 ml of triethylamine. The mixture was allowed to stand at room temperature overnight. With the addition of 100 ml of water, the reaction mixture was stirred at room temperature for 30 minutes. Thereafter, 600 ml of ethyl acetate was added and the organic layer was washed with aqueous sodium hydrogen carbonate and water in the order mentioned, and dried over anhydrous sodium sulfate. The solvent was removed under reduced pressure. In the above manner, N-methyl-N-propionyl-L-alanine methyl ester was obtained as a yellow oil.

NMR spectrum(CDCl$_3$) δ: 1.15(3H,t,J=7 Hz), 1.40(3H,d,J=7 Hz), 2.40(2H,q,J=7 Hz), 2.93(3H,s), 3.70(3H,s), 5.27(1H,q,J=7 Hz).

The above methyl ester was dissolved in 50 ml methanol-200 ml 1 N-aqueous sodium hydroxide and the solution was allowed to stand at room temperature for 2 hours. The methanol was removed under reduced pressure and the residual aqueous solution was extracted with chloroform. The aqueous solution was adjusted to pH 2 with concentrated hydrochloric acid under ice-cooling and extracted with ethyl acetate (150 ml×4). The extract was dried over anhydrous sodium sulfate. The solvent was removed under reduced pressure and the residual yellow oil was dissolved in ethyl acetate. Upon addition of hexane, colorless prisms separated out. These crystals were recrystallized from ethyl acetate-hexane. By the above procedure was obtained 14.7 g of colorless prisms of N-methyl-N-propionyl-L-alanine.

Elemental analysis, for $C_7H_{13}NO_3$: Calcd. C, 52.81; H, 8.23; N, 8.80: Found C, 52.77; H, 8.55; N, 8.81. $[\alpha]_D^{25} -70.2°$ (c=1, $H_2O$).
m.p. 108°-110° C.

NMR spectrum(DMSO-$d_6$) δ: 1.00(3H,t,J=7 Hz), 1.28(3H,d,J=7 Hz), 2.33(2H,q,J=7 Hz), 2.88(3H,s), 4.97(1H,q,J=7 Hz), 12.0(1H,br.)

EXAMPLE 25

26 g (0.17 mol) of N-methyl-L-alanine methyl ester hydrochloride and 25 g (0.23 mol) of isobutyryl chloride were dissolved in 200 ml of chloroform, and under ice-cooling, 80 ml of triethylamine was added dropwise over a period of 50 minutes. The mixture was stirred under ice-cooling for an additional hour and, then, at room temperature for 1.5 hours. An additional 10 ml of triethylamine was added to the reaction mixture and, following the addition of 50 ml of water, the mixture was stirred for a while. After 400 ml of ethyl acetate was added, the reaction mixture was washed with water, an aqueous solution of sodium hydrogen carbonate and a saturated aqueous solution of sodium chloride in the order mentioned, followed by drying over anhydrous sodium sulfate.

The solvent was removed under reduced pressure, whereupon N-isobutyryl-N-methyl-L-alanine methyl ester was obtained as a red oil.

NMR spectrum(CDCl$_3$) δ: 1.13(6H,d,J=7 Hz), 1.42(3H,d,J=7 Hz), 2.87(1H,m), 2.98(3H,s), 3.70(3H,s), 5.20(1H,q,J=7 Hz).

This ester was hydrolyzed with 170 ml of 1 N-aqueous sodium hydroxide in 100 ml of methanol and, then, after-treated in the manner described above. By the above procedure was obtained 18.1 g of colorless prisms of N-isobutyryl-N-methyl-L-alanine.

Elemental analysis, for $C_8H_{15}NO_3$: Calcd. C, 55.47; H, 8.73; N, 8.09: Found C, 55.44; H, 8.86; N, 8.06.
$[\alpha]_D^{25} -68.7°$ (c=1, H$_2$O)
m.p. 117°–118° C.

NMR spectrum(DMSO-d$_6$) δ: 1.00(6H,d,J=7 Hz), 1.28(3H,d,J=7 Hz), 2.87(1H,m), 2.93(3H,s), 4.93(1H,q,J=7 Hz), 12.5(1H,br.).

EXAMPLE 26

26 g (0.17 mol) of N-methyl-L-alanine methyl ester hydrochloride and 25 g (0.21 mol) of isovaleryl chloride were dissolved in 200 ml of chloroform, and under ice-cooling, 70 ml of triethylamine was added dropwise over a period of 30 minutes. The mixture was allowed to stand at room temperature for 3.5 hours, after which 20 ml of water was added. The mixture was stirred for 20 minutes and extracted with ethyl acetate (100 ml×4). The solvent was removed under reduced pressure, whereupon N-methyl-N-isovaleryl-L-alanine methyl ester was obtained as a brown-colored oil.

NMR spectrum(CDCl$_3$) δ: 0.98(6H,d,J=6 Hz), 1.40(3H,d,J=7 Hz), 1.0–1.6(1H,m), 2.26(2H,d,J=3 Hz), 2.97(3H, s), 3.70(3H,s), 5.24(1H,q,J=7 Hz).

This ester was dissolved in 100 ml methanol-180 ml 1 N-aqueous sodium hydroxide and the hydrolyzate mixture was treated as described above to recover 17.1 g colorless flakes of N-methyl-N-isovaleryl-L-alanine.

Elemental analysis, for $C_9H_{17}NO_3$: Calcd. C, 57.73; H, 9.15; N, 7.48: Found C, 57.85; H, 9.35; N, 7.33.
$[\alpha]_D^{25} -66.4°$ (c=1, H$_2$O)
m.p. 88°–89° C.

NMR spectrum(CDCl$_3$) δ: 0.95(6H,d,J=7.5 Hz), 1.0–1.2 (1H,m), 1.42(3H,d,J=7 Hz), 2.27(2H,m), 2.88(s) & 2.97(s) total 3H; 5.27(1H,q,J=7 Hz), 11.60(1H,s).

EXAMPLE 27

A culture of microorganisms producing antibiotic C-15003 (deposition No. IFO 13726, FERM-P 3992; ATCC 31281) on yeast extract-malt extract-agar slant was used to inoculate a 200 ml-conical flask containing 40 ml of a seed-culture medium (pH 7.0) composed of 2% glucose, 3% soluble starch, 1% raw soybean flour, 1% corn steep liquor, 0.5% polypeptone, 0.3% NaCl and 0.5% CaCO$_3$. The inoculated flask was incubated on a rotary shaker at 28° C. for 48 hours to prepare a seed culture.

A 0.5 ml portion of the above seed culture was transferred to a 200 ml conical flask containing 40 ml of a fermentation medium (pH 7.0) composed of 5% dextran, 3% corn steep liquor, 0.1% polypeptone and 0.5% CaCO$_3$, and the inoculated flask was incubated on a rotary shaker at 28° C. for 90 hours.

The resultant broth was assayed by the liquid dilution method using *Tetrahymena pyriformis W* as the assay organism and Antibiotic C-15003 P-3 as the standard. The production titer was found to be 25 μg/ml.

EXAMPLE 28

A 10 ml portion of the seed culture obtained in Example 27 was transferred to a 2 1-Sakaguchi flask containing 500 ml of the seed-culture medium and incubated on a reciprocating shaker at 28° C. for 48 hours. This culture, 500 ml, was transferred to a 50 l-tank of stainless steel containing 30 l of the seed-culture medium and the cultivation was carried out at 28° C., 30 l/min. aeration, 280 r.p.m. (½ DT) and internal pressure 1 kg/cm$^2$ and 48 hours. The resultant seed culture was used to inoculate a 200 l-tank of stainless steel containing 100 l of a fermentation medium similar to that used in Example 27, the rate of transfer being 10%. The cultivation was carried out at 28° C., 100 l/min. aeration, 200 r.p.m. (½ DT) and 1 kg/cm$^2$ internal pressure for 90 hours. The resultant broth as determined by the same assay method as that described in Example 27 showed a production titer of 25 μg/ml.

EXAMPLE 29

To 95 l of the culture broth obtained in Reference Example 28 was added 2 kg of Hyflosupercel (Johnes Manville Products, U.S.), followed by thorough stirring. The mixture was filtered on a filter press to obtain 85 l of filtrate and 32 kg of moist cells. The filtrate, 85 l, was extracted with 30 l of ethyl acetate under stirring. This procedure was repeated again. The ethyl acetate layers were combined, washed twice with 30 l portions of water, dried with the addition of 500 g of anhydrous sodium sulfate, and concentrated under reduced pressure to 200 ml. Following the addition of petroleum ether, the resultant precipitate was recovered by filtration (53 g). The resultant crude product I was stirred with 100 ml of ethyl acetate and the insolubles were filtered off. The filtrate was stirred with 10 g of silica gel (Merck, West Germany, 0.05–0.2 mm) and the ethyl acetate was removed under reduced pressure. The residue was applied to the top of a prepared column of silica gel (400 ml) and elutions were carried out with 500 ml of n-hexane, 500 ml of n-hexane-ethyl acetate (3:1), 500 ml of n-hexane-ethyl acetate (1:1), 500 ml of n-hexane-ethyl acetate (1:3), 500 ml of ethyl acetate and 1 l of ethyl acetate-methanol (50:1), the eluate being collected in 100 ml fractions. A 1 ml portion of each fraction was concentrated to dryness and, after the addition of 0.1 ml of ethyl acetate, spotted at a distance of 2.5 cm from the bottom edge of a silica gel-glass plate (Merck, West Germany, Kiesel/gel 60 F 254 0.25 mm 20×20). The development was carried out with a solvent mixture of ethyl acetate and methanol (19:1) across a dimension of about 17 cm. After development, ultraviolet detection was carried out and the fractions absorbing (2537 Å) in the neighborhood of Rf 0.6 to 0.65, i.e. fractions No. 23 to No. 28, were collected and concentrated under reduced pressure to about 20 ml. To this concentrate was added 150 ml of petroleum ether to recover 15 g of crude product II.

EXAMPLE 30

To 32 kg of the moist cells obtained in Example 29 was added 50 l of 70% acetone-water and the extraction was carried out with stirring for 3 hours. The extract was filtered on a filter press. Another extraction was carried out using 50 l of 70% acetone-water and the extract was similarly filtered. The filtrates were pooled and concentrated under reduced pressure to remove the acetone. The resultant aqueous solution was passed through a column of 5 l Diaion HP-10 (Mitsubishi Kasei) and, after the column was washed with 20 l of water and 50% methanol-water, elution was carried out with 90% methanol-water. The eluate was concentrated under reduced pressure to 3 l and this concentrate was shaken with 3 l of water and 3 l of ethyl acetate. This procedure was repeated again. The ethyl acetate layers were combined, rinsed with water, dried by the addition of anhydrous sodium sulfate and concentrated under reduced pressure to 200 ml. To this concentrate was added petroleum ether and the resultant precipitate was recovered by filtration (28 g). The crude product thus obtained was purified by a procedure similar to that described in Example 29 using a column of silica gel. By the above procedure was obtained 8.0 g of crude product II.

EXAMPLE 31

In 10 ml of ethyl acetate was dissolved 1.5 g of the crude product II obtained in Example 29 and the solution was stirred well with 4 g of silica gel (Merck, West Germany, 0.05–0.2 mm). The ethyl acetate was then removed under reduced pressure. The residue was applied to the top of a prepared column of 300 ml silica gel and, after the column was washed with 500 ml of chloroform, elution was carried out with 500 ml of chloroform-methanol (50:1), 500 ml of chloroform-methanol (20:1) and 500 ml of chloroform-methanol (10:1), the eluate being collected in 25 ml fractions. A 0.5 ml portion of each fraction was concentrated under reduced pressure and 0.05 ml of ethyl acetate was added. This concentrate, by way of sample, was subjected to thin-layer chromatography on silica gel (developing solvent: chloroform-methanol=9:1). The fractions No. 39 and No. 40 which absorbed at 2537 Å in Rf 0.50 to 0.60 were collected and concentrated to dryness under reduced pressure. To this concentrate was added 2 ml of ethyl acetate and the mixture was allowed to stand. By the above procedure was obtained 150 mg crystals of Antibiotic C-15003.

The crystalline Antibiotic C-15003 obtained above, 150 mg, was dissolved in 15 ml of methanol, and in this solution were dissolved 300 mg of sodium chloride and 15 ml of water. 200 ml of Diaion HP-10 (Mitsubishi Kasei) was packed into a column with a diameter of 1.8 cm and the column was calibrated with 600 ml of 50% methanol-water containing 5% of sodium chloride. The sample solution prepared above was passed through the column and, after 300 ml of 60% methanol-water containing 5% of sodium chloride was passed, gradient elution was carried out between 1.5 l of 60% methanol-water containing 5% of sodium chloride and 1.5 l of 95% methanol-water. The eluate was collected in 15 ml fractions and development and detection were carried out by silica gel TLC. C-15003P-3 occurred in fractions No. 145 to No. 153; C-15003 P-3' and P-4 in fractions No. 167 to No. 180; and C-15003 P-4 in fractions No. 185 to No. 190. Each group of fractions was collected, concentrated and dissolved by the addition of 50 ml water-100 ml ethyl acetate. The solution was put in a separatory funnel and, after shaking, the water layer was separated. After washing twice with 50 ml portions of water, the ethyl acetate layer was dried over anhydrous sodium sulfate and concentrated. On standing, the corresponding crystals separated out. These crystals were recovered by filtration and dried.

| C-15003 P-3 | 70 mg |
|---|---|
| C-15003 P-3', P-4 | 18 mg |
| C-15003 P-4 | 15 mg |

18 mg of the C-15003 P-3'-P-4 mixed crystals were dissolved in 0.3 ml of ethyl acetate and the solution was linearly applied at a distance of 2.5 cm from the lower edge of each of three silica gel-glass plates (Merck, West Germany, Kieselgel 60F 254 0.25 mm, 20×20 cm).

The chromatograms were developed with ethyl acetatemethanol (19:1). After development across a dimension of about 18 cm, the Rf 0.63 (P-4) and Rf 0.65 (P-3') zones were scraped off and independently extracted twice with ethyl acetate containing a small amount of water. The ethyl acetate extract was washed with water, dried over anhydrous sodium sulfate, concentrated under reduced pressure and allowed to stand. Thus, 10 mg of C-15003 P-4 and 3 mg of C-15003 P-3' were obtained from Rf 0.68 and Rf 0.65, respectively.

EXAMPLE 32

In 1 ml of tetrahydrofuran was dissolved 15 mg of the Antibiotic C-15003 crystals obtained in Example 31 and the solution was cooled to $-5°$ C. Following the addition of 12 mg of lithium aluminum hydride, the mixture was allowed to stand for 2 hours. Then, after the addition of 0.5 m of 1% $H_2SO_4$ in water, the reaction mixture was extracted with 2 ml of ethyl acetate. The ethyl acetate layer was washed with water, dried by the addition of anhydrous sodium sulfate and concentrated under reduced pressure. Preparative TLC was carried out on silica gel with ethyl acetate/methanol=19/1 and the absorbing zone in the neighborhood of Rf 0.25 to 0.3 was scraped off, extracted with ethyl acetate containing a small amount of water, washed with water, dried over anhydrous sodium sulfate and concentrated under reduced pressure. The resultant crystals were recovered by filtration and dried. By the above procedure was obtained 10 mg of maytansinol, m.p. 174° C.

Elemental analysis, for $C_{28}H_{37}ClN_2O_8$: Calcd. C, 59.52; H, 6.60, N, 4.96; Cl, 6.27: Found C, 59.65; H, 6.58; N, 5.02; Cl, 6.21.

IR: 1715, 1670, 1580($cm^{-1}$)

UV (nm). 232(32750), 244(sh. 30850), 252(31650), 281(5750), 288(5700).

The properties of this product are in agreement with those of maytansinol.

The yields and reaction conditions (e.g. temperature, time, etc.) mentioned in the above examples and reference examples may be improved by a repetition of trials.

Melting points are determined on a Yanagimoto MP-S3 melting point apparatus (Yanagimoto Seisakusho, Kyoto, Japan), ultraviolet absorption spectra on a Hitachi ESP-3T recording spectrophotometer, nuclear magnetic resonance spectra on a Varian EM-390 90 MHz NMR spectrometer and mass spectra on a JEOL JMS-01SC mass-spectrometer.

Compound A was dissolved in ethyl acetate-ether and this solution was left to stand in a fridge to give crystalline compound A, which was further recrystallized once from ethyl acetate-ether, then twice from methylene chloride-ether to give crystals of compound A: colorless plates, m.p. 191°–195° C. (decomposition).

The compound B crystallized when a chloroform solution of compound B was treated with ether. The crystals thus obtained were recrystallized further twice from the same solvent system to give crystals of compound B, melting at 155°–178° C. (gradually decomposed).

A solution of compound C in small amount of ethyl acetate separated crystals of compound C while being left to stand at room temperature. The crystals were collected and recrystallized from dichloromethane-ether to give crystals of compound C: colorless needles, melting at 185°–189° C. (with slight decomposition).

A solution of compound D in small amount of ethyl acetate gave crystals of compound D, which were recrystallized from dichloromethane-ether to give crystals of compound D: colorless needles melting at 192°–197° C. (decomposition).

A solution of compound E in small amount of ethyl acetate gave crystals, which were recrystallized from dichloromethane-ether to give crystals of compound E: colorless needles melting at 185°–187° C. (decomposition).

A solution of compound F in small amount of ethyl acetate-ether gave crystals which were recrystallized from dichloromethane-ether to give crystals of compound F: colorless needles melting at 195°–198° C. (decomposition).

What is claimed is:

1. A method of producing a maytansinoid of the formula:

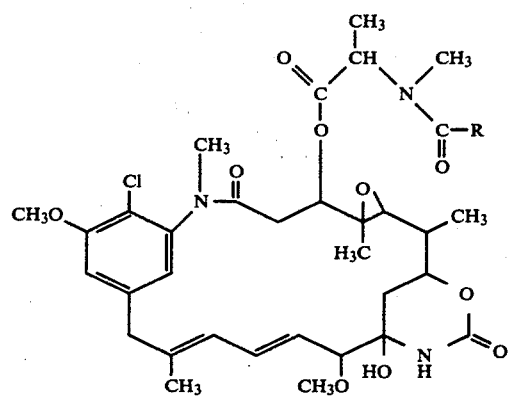

wherein R is lower alkyl, which comprises:
   (a) treating a compound of the formula

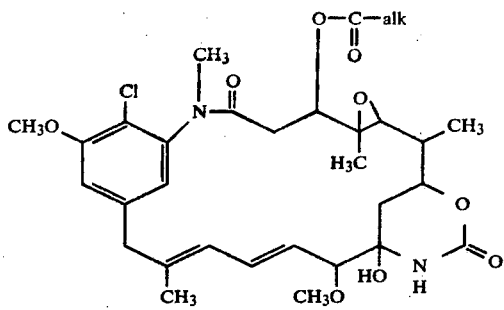

wherein alk is

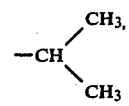

—CH$_2$CH$_2$CH$_3$ or

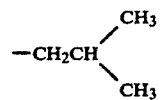

under conditions of reductive hydrolysis to yield maytinsinol; and
   (b) contacting the maytansinol with an acid of the formula

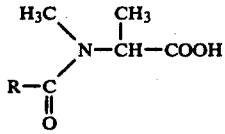

wherein R is lower alkyl, in the presence of a carbodiimide to yield said maytansinoid.

2. A method of claim 1, wherein R is methyl.
3. A method of claim 1, wherein said acid has the L-configuration.
4. A method of claim 1, wherein said carbodiimide is dicyclohexylcarbodiimide.
5. A method of claim 1, wherein said step (b) is conducted in the presence of a catalyst capable of enhancing the acylation of maytansinol.
6. A method of claim 5, wherein said catalyst is an acid or base catalyst.
7. A method of claim 5, wherein said catalyst is a Lewis acid, a strong organic acid, a strong inorganic acid, an acidic ion exchange resin, an organic amine, an alkali metal halide or a salt of organic acid.
8. A method of claim 5, wherein the catalyst is anhydrous zinc chloride, anhydrous aluminum chloride, anhydrous ferric chloride, titanium tetrachloride, stannic tetrachloride, antimony pentachloride, cobaltic chloride, cupric chloride, boron trifluoride etherate, sulfuric acid, perchloric acid, hydrogen chloride, hydrogen bromide, benzenesulfonic acid, p-toluenesulfonic acid, trifluoroacetic acid, trichloroacetic acid, pyridine, α-, β- or γ-picoline, 2,6-lutidine, 4-dimethylaminopyridine, dimethylaniline, diethylaniline, triethylamine, N-methylmorpholine, potassium fluoride, anhydrous lithium iodide or sodium acetate.
9. A method of claim 5, wherein the catalyst is anhydrous zinc chloride.
10. A method of claim 5, wherein said acid is employed in an amount of about 1 to about 30 molar equivalents to maytansinol.
11. A method of claim 5, wherein said acid is employed in an amount of about 1 to about 6 molar equivalents to maytansinol.

* * * * *